United States Patent
Tamano

(10) Patent No.: US 9,261,458 B2
(45) Date of Patent: Feb. 16, 2016

(54) MICROSCOPE SYSTEM AND METHOD FOR MEASURING REFRACTIVE INDEX OF SAMPLE

(71) Applicant: OLYMPUS CORPORATION, Shibuya-ku, Tokyo (JP)

(72) Inventor: Shingo Tamano, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 14/315,221

(22) Filed: Jun. 25, 2014

(65) Prior Publication Data

US 2015/0015871 A1    Jan. 15, 2015

(30) Foreign Application Priority Data

Jul. 9, 2013    (JP) ................. 2013-143905

(51) Int. Cl.
| | |
|---|---|
| *G01N 21/41* | (2006.01) |
| *G02B 21/00* | (2006.01) |
| *G02B 21/02* | (2006.01) |
| *G02B 21/14* | (2006.01) |
| *G02B 26/06* | (2006.01) |

(52) U.S. Cl.
CPC ............ *G01N 21/41* (2013.01); *G02B 21/02* (2013.01); *G02B 21/14* (2013.01); *G02B 26/06* (2013.01)

(58) Field of Classification Search
USPC ............ 356/128–137, 632; 250/208.5, 201.3; 359/368
See application file for complete search history.

(56) References Cited

U.S. PATENT DOCUMENTS

| | | | |
|---|---|---|---|
| 6,771,417 B1 | 8/2004 | Wolleschensky et al. | |
| 7,224,645 B2 * | 5/2007 | Ando et al. ............... | 369/44.23 |
| 2002/0154398 A1 | 10/2002 | Wolleschensky et al. | |
| 2006/0098213 A1 * | 5/2006 | Itoh et al. ...................... | 356/632 |
| 2007/0007428 A1 * | 1/2007 | Ri .............................. | 250/201.3 |
| 2007/0153298 A1 * | 7/2007 | Fukui ........................... | 356/632 |
| 2009/0046298 A1 * | 2/2009 | Betzig ......................... | 356/521 |
| 2009/0125242 A1 * | 5/2009 | Choi et al. ..................... | 702/19 |
| 2009/0263002 A1 * | 10/2009 | Cremer et al. ................ | 382/133 |
| 2014/0233094 A1 * | 8/2014 | Ue et al. ....................... | 359/368 |
| 2014/0374575 A1 * | 12/2014 | Takesue et al. ............. | 250/208.5 |

FOREIGN PATENT DOCUMENTS

| | | |
|---|---|---|
| JP | 11101942 A | 4/1999 |
| JP | 2005224841 A | 8/2005 |

* cited by examiner

*Primary Examiner* — Sang Nguyen
(74) *Attorney, Agent, or Firm* — Holtz, Holtz & Volek PC

(57) ABSTRACT

A microscope system includes: a wavefront modulator that modulates a wavefront of light from a light source; an objective that irradiates a sample with light whose wavefront has been modulated by the wavefront modulator; a spherical aberration corrector that corrects spherical aberration caused by a difference between a refractive index of a medium between the objective and the sample and a refractive index of the sample; a refractive index calculator that calculates, for each wavelength of the light from the light source, an average refractive index of a medium between the objective and a condensing position of light emitted from the objective on the basis of an amount of the corrected spherical aberration; and a controller that controls the wavefront modulator to correct chromatic aberration calculated on the basis of the calculated average refractive index for each wavelength.

7 Claims, 18 Drawing Sheets

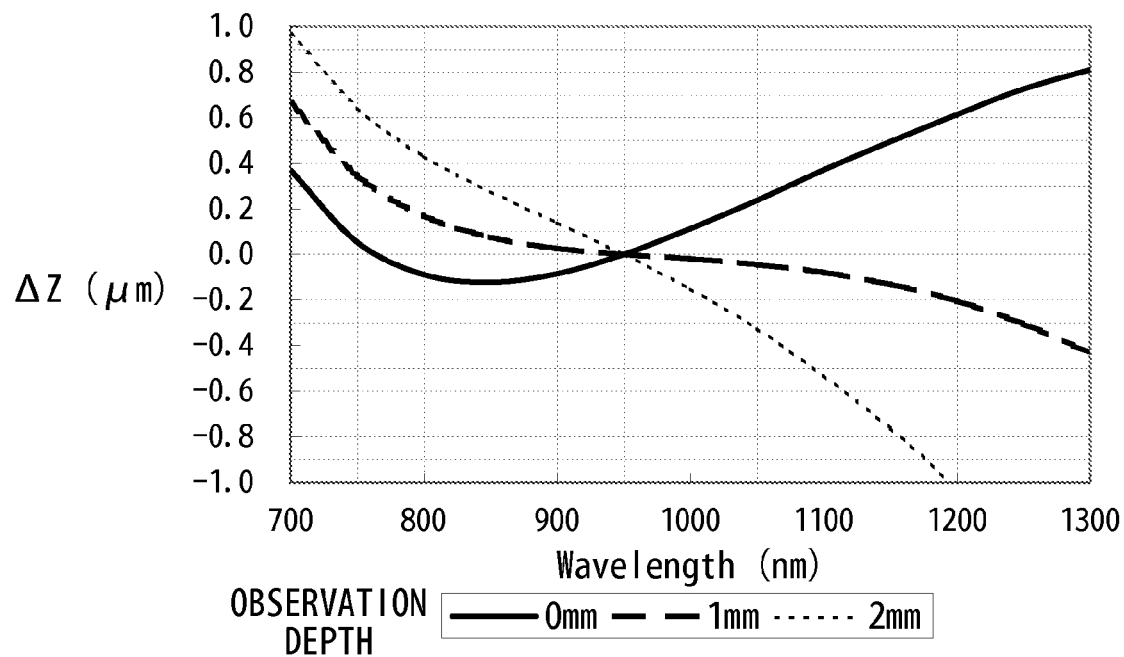
F I G. 1

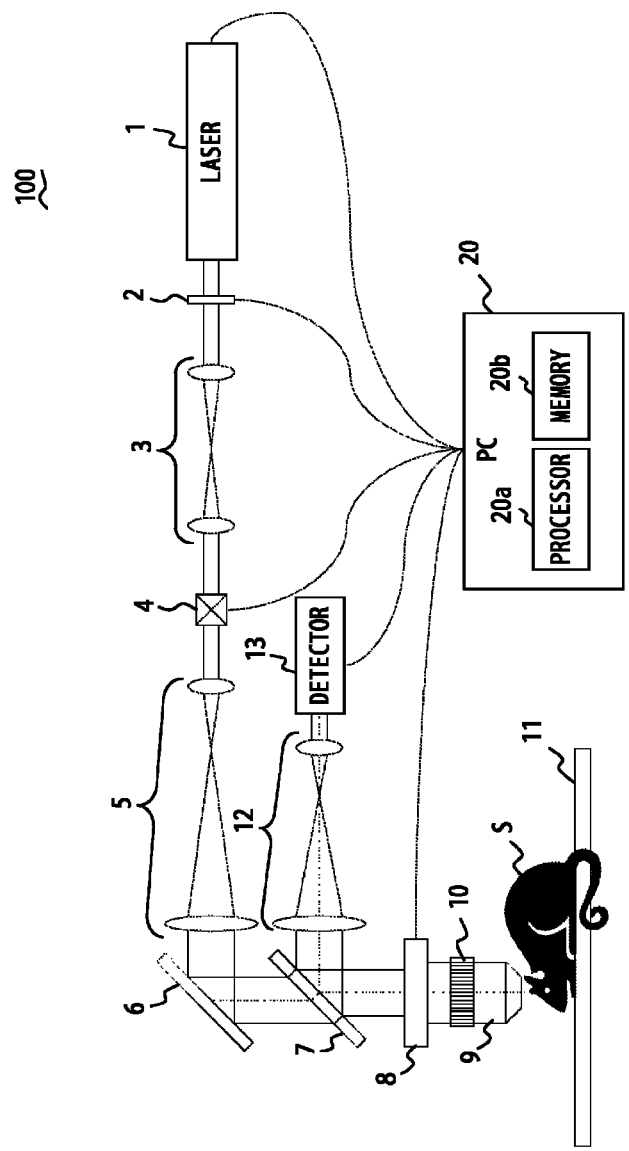
F I G. 2

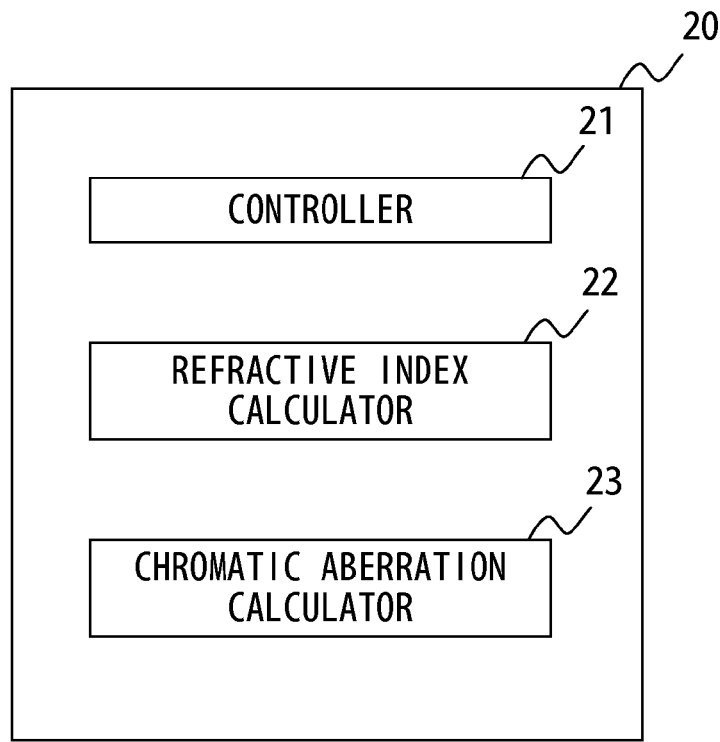
F I G. 3

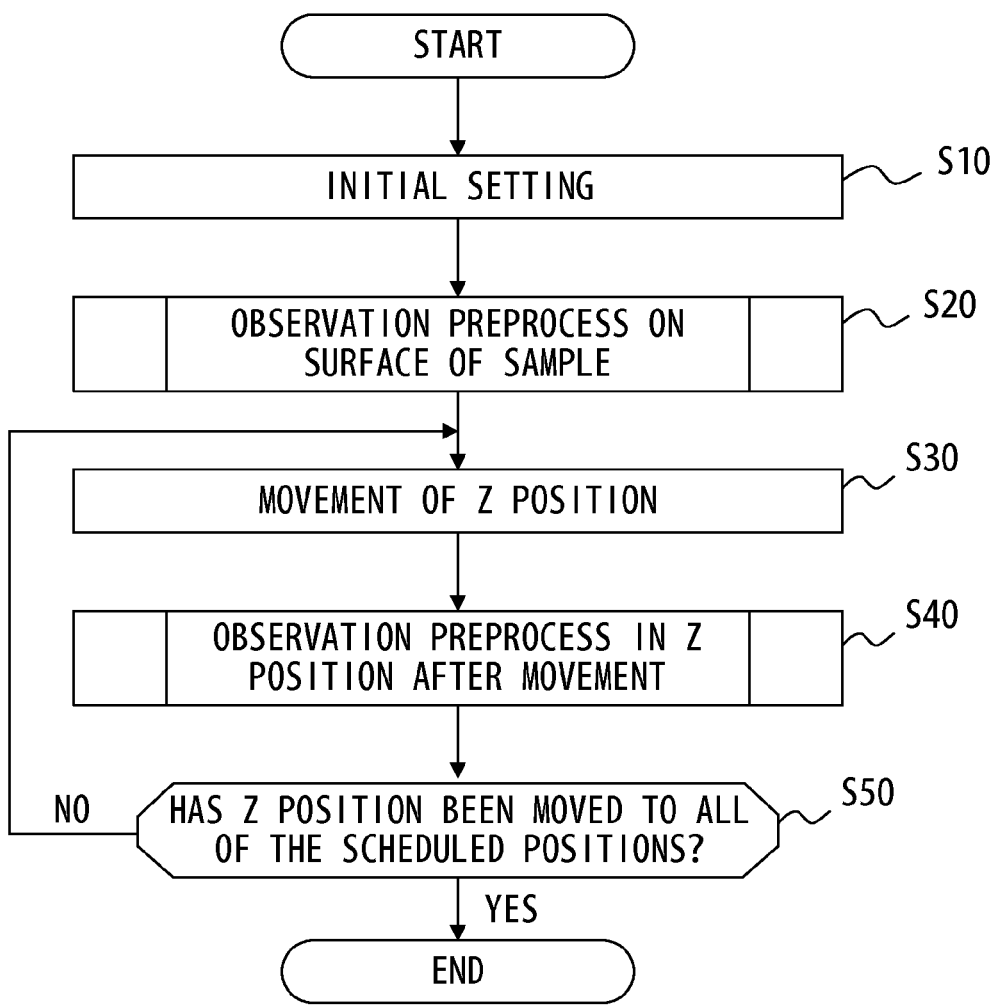
F I G. 4

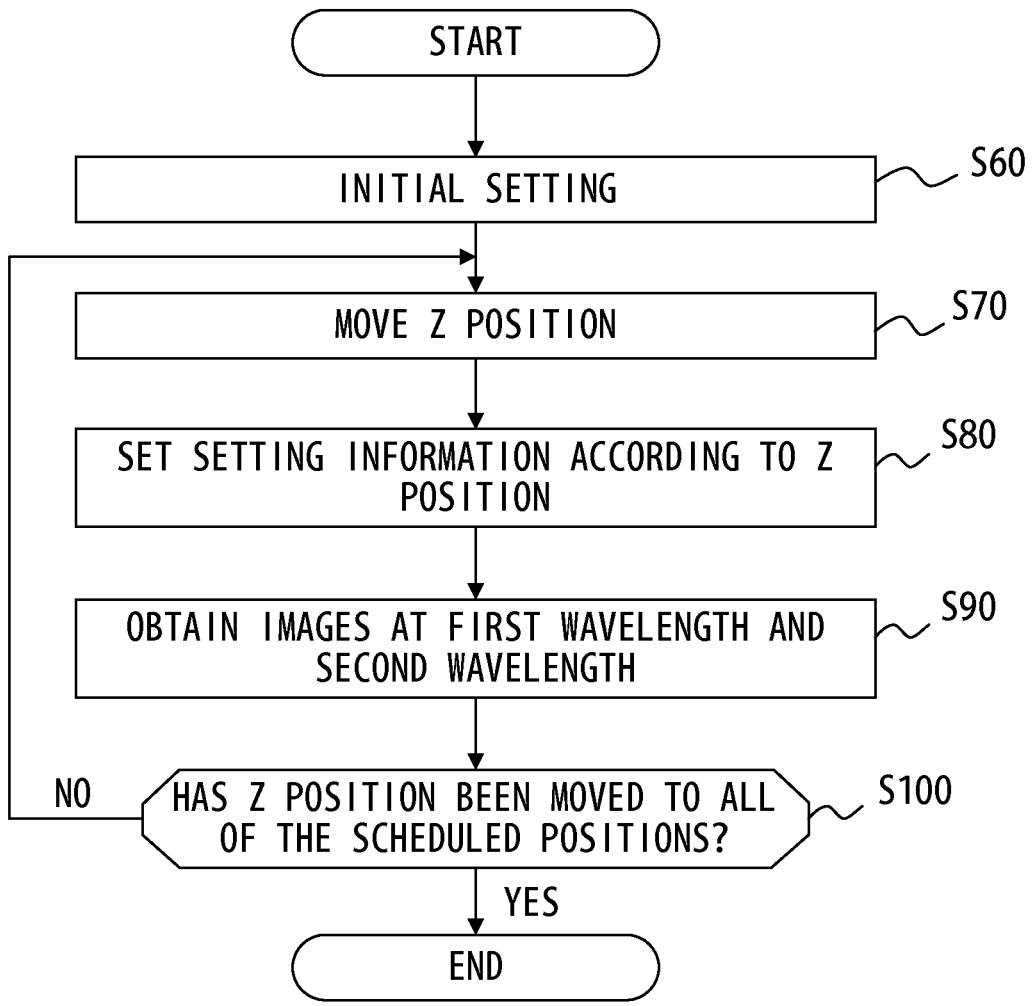
F I G. 7

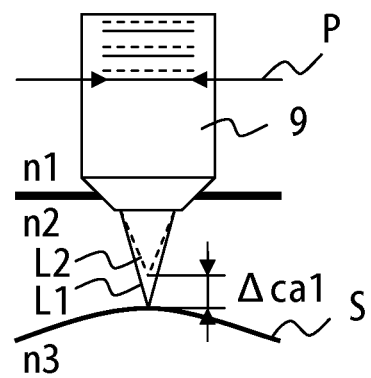
F I G. 8 A

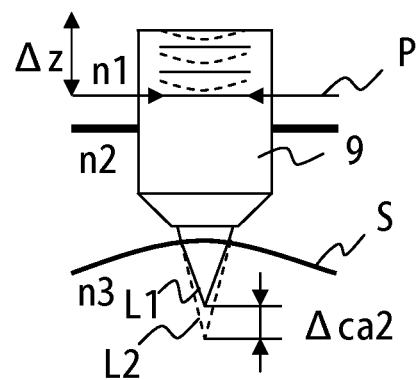
F I G. 8 C

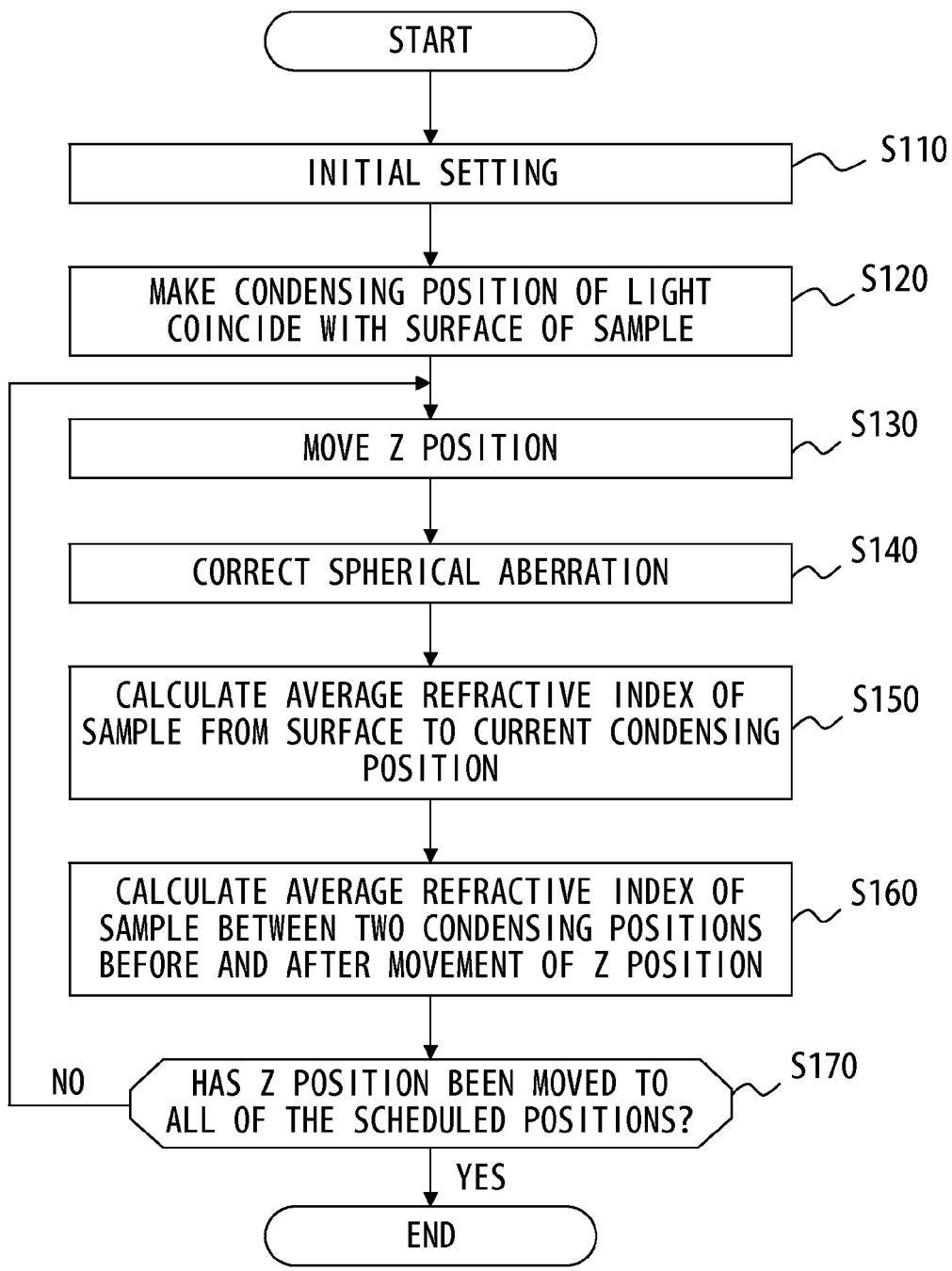
F I G. 1 0

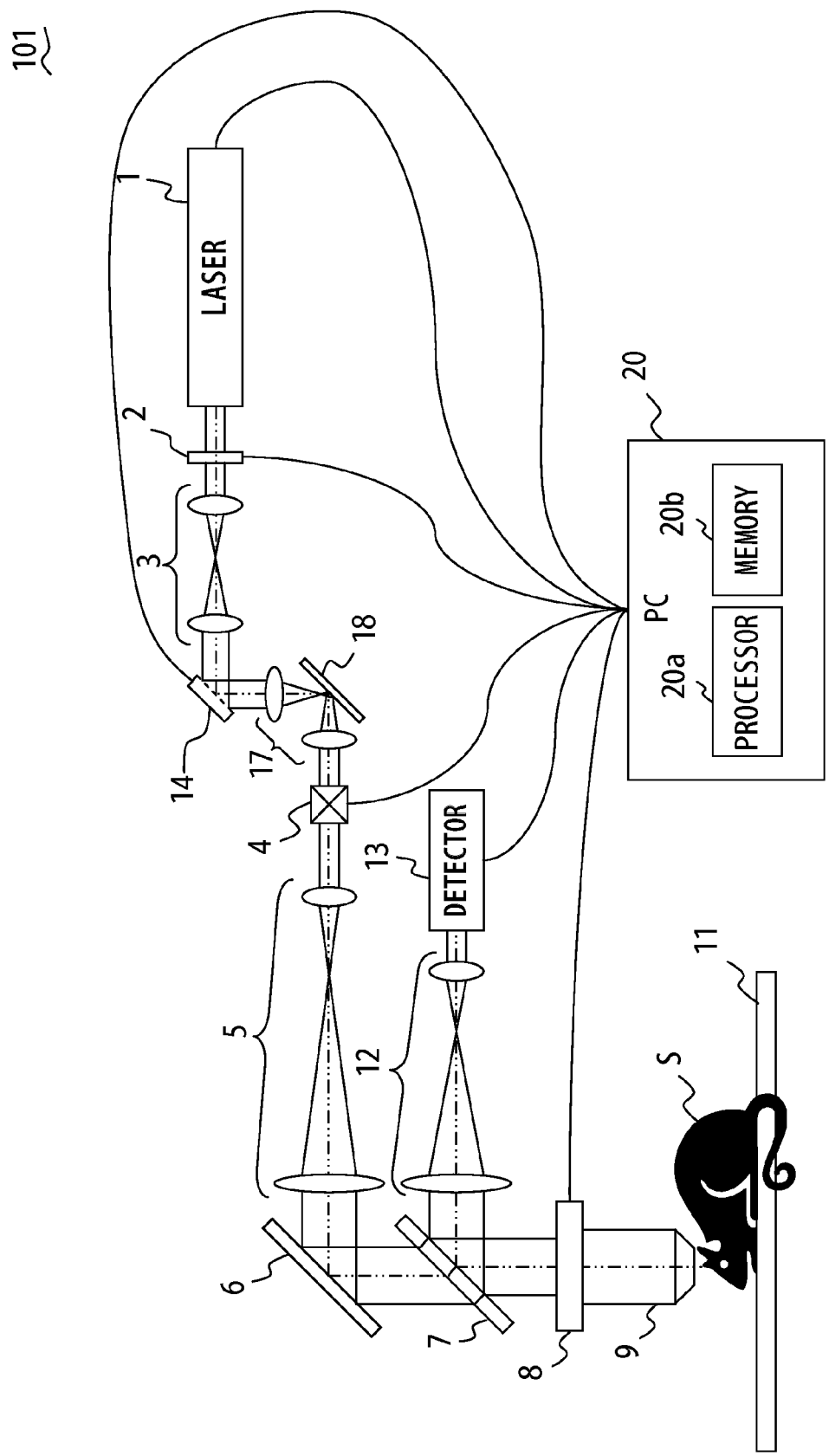
F I G. 11

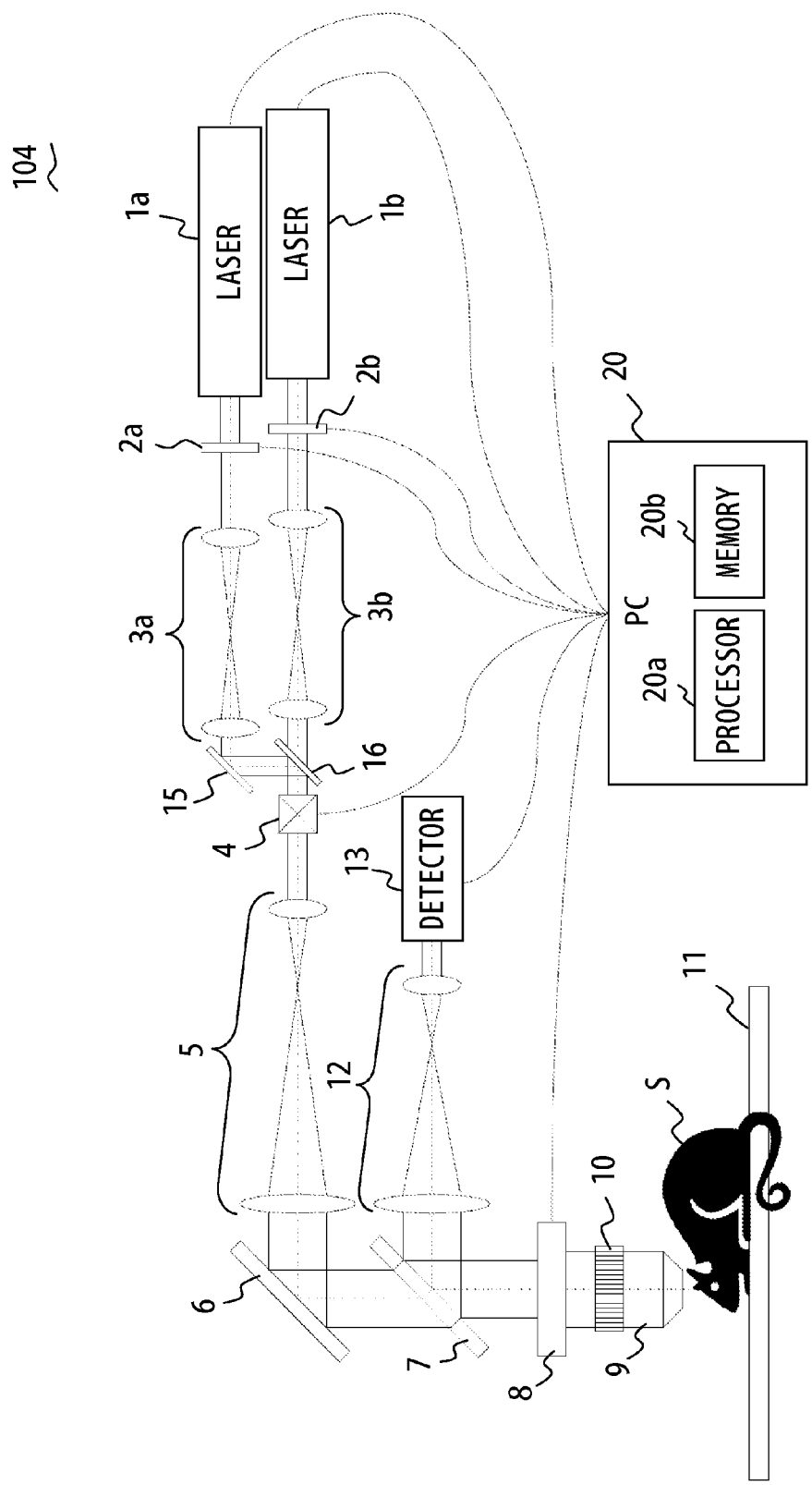
F I G. 14

MICROSCOPE SYSTEM AND METHOD FOR MEASURING REFRACTIVE INDEX OF SAMPLE

CROSS REFERENCE TO RELATED APPLICATIONS

This application is based upon and claims the benefit of priority from prior Japanese Patent Application No. 2013-143905, filed Jul. 9, 2013, the entire contents of which are incorporated herein by this reference.

BACKGROUND OF THE INVENTION

1. Field of the Invention

The present invention relates to a microscope system and a method for measuring a refractive index of a sample.

2. Description of the Related Art

A fluorescence observation method using a multi-photon excitation microscope is attracting attention as a method for observing a biological sample. The multi-photon excitation microscope excites a sample with excitation light having a wavelength longer than that of excitation light of a single-photon excitation microscope. As light having a long wavelength is hardly scattered, the multi-photon excitation microscope enables making excitation light reach a deep portion of a sample that easily scatters light, such as a biological sample, and as a result, the multi-photon excitation microscope enables observing a deeper portion of a sample than the single-photon excitation microscope.

Japanese Laid-Open Patent Publication No. 11-101942 discloses a microscope including a wavefront modulator on an optical path. Japanese Laid-Open Patent Publication No. 2005-224841 discloses a laser beam machining device, and describes that chromatic aberration is generated by the dispersion of a material.

SUMMARY OF THE INVENTION

One aspect of the present invention provides a microscope system that includes: a wavefront modulator that modulates a wavefront of light from a light source; an objective that irradiates a sample with the light whose wavefront has been modulated by the wavefront modulator; a spherical aberration corrector that corrects spherical aberration caused by a difference between a refractive index of a medium between the objective and the sample and a refractive index of the sample; a refractive index calculator that calculates an average refractive index of a medium between the objective and a condensing position of light emitted from the objective on the basis of an amount of the spherical aberration corrected by the spherical aberration corrector for each wavelength of the light from the light source; and a controller that controls the wavefront modulator to correct chromatic aberration calculated on the basis of the average refractive index for each wavelength calculated by the refractive index calculator.

Another aspect of the present invention provides a method for measuring a refractive index of a sample with a microscope system, the method including: relatively moving an objective in an optical axis direction with respect to the sample so as to make a condensing position of light emitted from the objective of the microscope system coincide with a surface of the sample; relatively moving the objective in the optical axis direction with respect to the sample so as to move the condensing position of the light emitted from the objective inside the sample; correcting spherical aberration inside the sample; and calculating the refractive index of the sample between the surface of the sample and the condensing position inside the sample on the basis of an amount of the corrected spherical aberration.

BRIEF DESCRIPTION OF THE DRAWINGS

The present invention will be more apparent from the following detailed description when the accompanying drawings are referenced.

FIG. 1 illustrates a deviation amount of a condensing position with respect to a reference wavelength.

FIG. 2 illustrates a configuration of a microscope system according to Embodiment 1 of the present invention.

FIG. 3 is a functional block diagram of a control device of the microscope system according to Embodiment 1 of the present invention.

FIG. 4 is a flowchart of an observation preprocess performed in the microscope system according to Embodiment 1 of the present invention.

FIG. 7 is a flowchart of an observation process performed after the observation preprocess in the microscope system according to Embodiment 1 of the present invention.

FIG. 8A illustrates a state in which chromatic aberration has not been corrected on the surface of a sample.

FIG. 8C illustrates a state in which chromatic aberration has not been corrected inside a sample.

FIG. 10 is a flowchart of a process of measuring a refractive index of a sample performed in the microscope system according to Embodiment 1 of the present invention.

FIG. 11 illustrates a configuration of a microscope system according to Embodiment 2 of the present invention.

FIG. 14 illustrates a configuration of a microscope system according to Embodiment 5 of the present invention.

DESCRIPTION OF THE EMBODIMENTS

Figure 5:
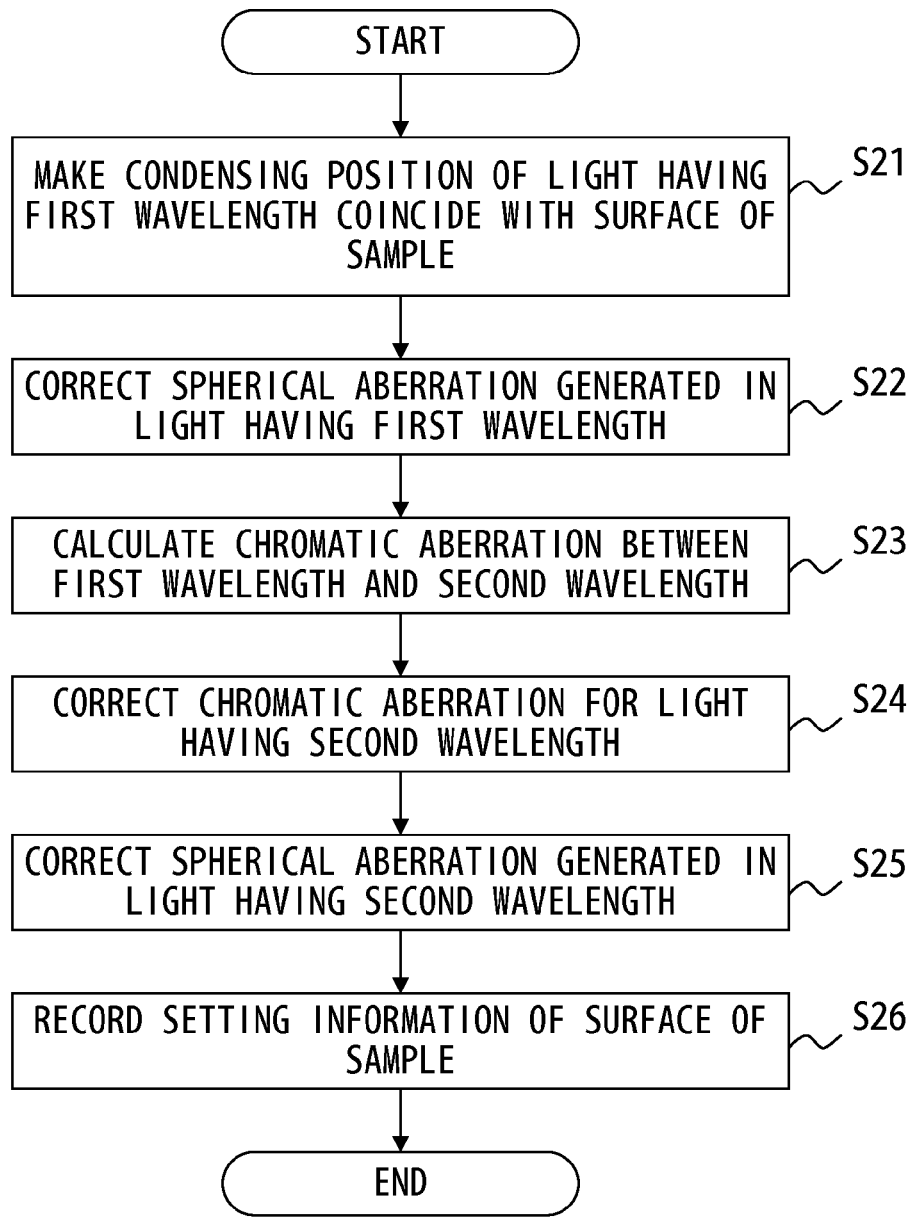
FIG. 5 is a flowchart of an observation preprocess on a surface of a sample illustrated in FIG. 4.

In a multi-photon excitation microscope, a plurality of light beams having excitation wavelengths different from each other are used depending on a fluorescent material. When a light beam having a different wavelength is used, a different amount of chromatic aberration with respect to a light beam having a reference wavelength is generated. Therefore, when an excitation wavelength is changed depending on a fluorescent material, a condensing position is sometimes changed. In order to avoid this, chromatic aberration generated between used wavelengths may be corrected. As a result, a condensing position can be kept constant without depending on a wavelength.

However, the countermeasure above can be taken only when a refractive index of a medium between an objective and a condensing position is known and therefore chromatic aberration is also known (for example, a case in which the surface of a sample is observed, or other cases). When the inside of a sample is observed (for example, a case in which a deep portion of a brain is observed in vivo, or other cases), a refractive index of a sample is generally unknown, and chromatic aberration is also unknown. Therefore, it is difficult to keep a condensing position constant without depending on a wavelength by correcting the chromatic aberration.

The problem as described above is particularly noticeable in a multi-photon excitation microscope with which a deep portion of a sample is observable. This is because, as illustrated in FIG. 1, when the depth of an observation plane (the observation depth) of a sample is changed even when light having the same wavelength is used, a different amount of chromatic aberration with respect to light having a reference wavelength is generated, and a condensing position is changed. Also in the other microscopes, when the inside of a sample whose refractive index is unknown is observed, there is a similar problem.

Described below are embodiments of the present invention.

Embodiment 1

FIG. 2 illustrates a configuration of a microscope system 100 according to this embodiment. The microscope system 100 illustrated in FIG. 2 includes a two-photon excitation microscope, a personal computer (PC) 20 that is a control device that controls the two-photon excitation microscope, a monitor and an input device not illustrated that are connected to the PC 20.

The two-photon excitation microscope includes a laser 1, a wavefront modulator 2, a beam expander 3, a galvano-scanner 4, a pupil relay optical system 5, a mirror 6, a dichroic mirror 7, a revolver 8, an objective 9 including a correction collar 10, a stage 11 on which a sample S is arranged, a detection optical system 12, and a detector 13, as illustrated in FIG. 2.

The laser 1 is a laser light source that switches a plurality of laser beams having different wavelengths and emits the switched laser beam, and is a so-called wavelength variable laser. The laser 1 is, for example, a titanium sapphire laser.

The wavefront modulator 2 is a wavefront modulator that modulates a wavefront of a laser beam from the laser 1, and is arranged in a position optically conjugate to a pupil position of the objective 9 (hereinafter referred to as a "pupil conjugate position). The wavefront modulator 2 is a liquid crystal device such as an LCOS (Liquid Crystal On Silicon).

The beam expander 3 is an optical system that changes a beam diameter of a laser beam whose wavefront has been modulated by the wavefront modulator 2. The beam expander 3 is configured to project an image of the galvano-scanner 4 to the wavefront modulator 2.

The galvano-scanner 4 is a mirror that changes a direction in which a laser beam deflects so as to move a condensing position of a laser beam emitted from the objective 9 in XY directions orthogonal to an optical axis of the objective 9. Namely, the galvano-scanner 4 is an XY scanner that scans the sample S with a laser beam in the XY directions orthogonal to the optical axis of the objective 9. The galvano-scanner 4 is arranged in a pupil conjugate position that is a position optically conjugate to a position of the wavefront modulator 2.

The pupil relay optical system 5 is an optical system that projects an image of the galvano-scanner 4 in a pupil position of the objective 9.

The mirror 6 is a reflection mirror that reflects a laser beam toward the objective 9.

The dichroic mirror 7 is a mirror that has optical characteristics of transmitting a laser beam from the laser 1 and reflecting fluorescence from the sample S, and is an optical path branching unit that branches an illumination optical path and a detection optical path by separating the laser beam from the fluorescence.

The revolver 8 is a device that holds the objective 9 so as to be movable in the optical axis direction of the objective 9 (Z direction). Namely, the revolver 8 is a Z scanner that relatively moves the objective 9 in the optical axis direction with respect to the sample S so as to change a condensing position of a laser beam emitted from the objective 9. The stage 11 may be moved in the optical axis direction instead of the revolver 8 and the objective 9. In this case, the stage 11 is the Z scanner that changes the condensing position of the laser beam emitted from the objective 9.

The objective 9 is an objective that irradiates the sample S with a laser beam whose wavefront has been modulated by the wavefront modulator 2 and includes a correction collar 10. In this example, the objective 9 is an immersion objective used in a state in which a space between the objective 9 and the sample S is filled with immersion liquid, but the microscope system 100 may include a dry objective instead of the immersion objective.

The correction collar 10 is a mechanism that moves apart of lenses comprised in the objective 9 in the optical axis direction. The correction lens 10 is a spherical aberration corrector that corrects spherical aberration caused by a difference between a refractive index of a medium between the objective 9 and the sample S (in this example, immersion liquid) and a refractive index of the sample S (spherical aberration caused by a so-called index mismatch).

The detection optical system 12 is an optical system that projects an image of a pupil of the objective 9 to a light receiving surface of the detector 13.

The detector 13 is a photodetector that detects fluorescence from the sample S. The detector 13 is, for example, a photomultiplier tube (PMT).

The PC 20 is connected to at least the laser 1, the wavefront modulator 2, the galvano-scanner 4, the revolver 8, and the detector 13 from among components of the two-photon excitation microscope. The PC 20 is a computer including a memory 20b and a processor 20a, and executes a control program stored beforehand. As a result of this, as illustrated in FIG. 3, the processor 20a functions as a controller 21 that controls the components of the two-photon excitation microscope, a refractive index calculator 22 that calculates an average refractive index of a medium between the objective 9 and a condensing position of light emitted from the objective 9, and a chromatic aberration calculator 23 that calculates chromatic aberration generated between wavelengths.

In the microscope system 100 configured as described above, the wavefront of the laser beam emitted from the laser 1 is modulated by the wavefront modulator 2, the beam diameter of the laser beam is changed by the beam expander 3, and then the laser beam is made incident on the galvano-scanner 4. The laser beam deflected by the galvano-scanner 4 is made incident on the objective 9 via the pupil relay optical system 5, the mirror 6, and the dichroic mirror 7. The laser beam incident on the objective 9 is condensed by the objective 9, and is applied to the sample S.

Fluorescence generated from the sample S that has been irradiated with the laser beam is made incident on the dichroic mirror 7 via the objective 9. The fluorescence is reflected by the dichroic mirror 7, and is detected by the detector 13 via the detection optical system 12. The detector 13 converts the fluorescence into an electrical signal, and outputs the electrical signal to the PC 20. Then, the PC 20 generates an image of the sample S from the electrical signal from the detector 13 and scanning position information of the galvano-scanner 4, and displays the image on a monitor not illustrated.

Figure 6:
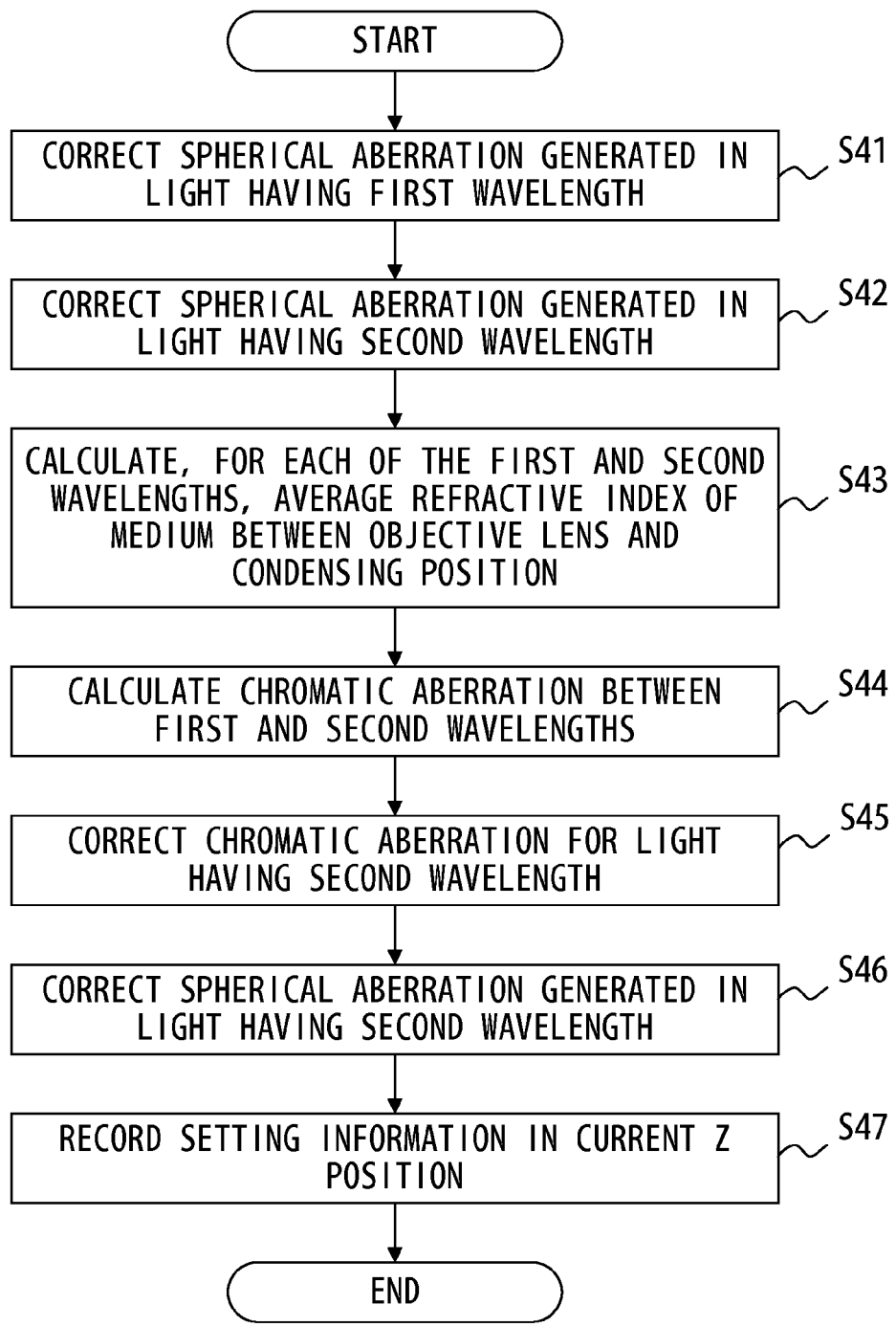
FIG. 6 is a flowchart of an observation preprocess in a Z position after the movement illustrated in FIG. 4.

FIG. 4 is a flowchart of an observation preprocess performed in the microscope system 100 according to this embodiment. FIG. 5 is a flowchart of an observation preprocess on a surface of a sample illustrated in FIG. 4, and FIG. 6 is a flowchart of an observation preprocess in a Z position after the movement illustrated in FIG. 4. FIG. 7 is a flowchart of an observation process performed after the observation preprocess in the microscope system 100 according to this embodiment. With reference to the flowcharts in FIG. 4 to FIG. 7, a method for observing the same position inside the sample S at two different wavelengths.

When the observation preprocess is started, the PC 20 obtains initial conditions input by a user, and sets the initial conditions (step S10 of FIG. 4). Here, two excitation wavelengths (a first wavelength $\lambda 1$ and a second wavelength $\lambda 2$) used in the observation, a refractive index n1 of immersion liquid, information of a used objective (a working distance WD, lens data, and the like), a pitch $\Delta z$ at the time of moving a Z position in the optical axis direction, a thickness d of a sample, and the like are set as the initial conditions. The refractive index n1 of immersion liquid is set for each excitation wavelength. Hereinafter, a refractive index of immersion liquid at the first wavelength is referred to as n21, and a refractive index of immersion liquid at the second wavelength is referred to as n22.

Next, the PC 20 performs an observation preprocess on a surface of a sample S (step S20 of FIG. 4). Specifically, six processes illustrated in FIG. 5 are performed.

First, the PC 20 makes a condensing position of light L1 having the first wavelength $\lambda 1$ coincide with the surface of the sample S (step S21 of FIG. 5). Here, the PC 20 controls the laser 1 to emit the light L1 having the first wavelength $\lambda 1$. Further, the PC 20 controls the revolver 8 to relatively move the objective 9 in the optical axis direction with respect to the sample S, and makes the condensing position of the light L1 having the first wavelength $\lambda 1$ emitted from the objective 9 coincide with the surface of the sample S. The revolver 8 may be controlled manually via the PC 20 while a user is viewing an image of the sample S displayed on a monitor, or the PC 20 may control the revolver 8 automatically using an auto-focus technique.

FIG. 8A illustrates a state in which a process of step S21 has been completed. Here, light L1 (a solid line) is light having the first wavelength $\lambda 1$, and light L2 (a broken line) is light having the second wavelength $\lambda 2$. In addition, n1 (=1) is a refractive index of air, n2 is a refractive index of immersion liquid, and n3 is a refractive index of the sample S, and they normally have a relation of n1<n2<n3. In step S21, a laser beam is not modulated by the wavefront modulator 2. Therefore, as illustrated in FIG. 8A, a laser beam having a linear wavefront is made incident on a pupil P of the objective 9.

The PC 20 corrects spherical aberration generated in the light L1 having the first wavelength $\lambda 1$ (step S22 of FIG. 5). Here, in a state in which the laser 1 continuously emits the light L1 having the first wavelength $\lambda 1$, a user rotates the correction collar 10 while viewing the image of the sample S displayed on the monitor so as to correct the spherical aberration. Then, the user inputs a rotation angle $\theta 1$ of the correction collar 10 in a state in which the spherical aberration has been corrected to the PC 20 by using an input device. When the PC 20 is configured to control the correction collar 10, the PC 20 may control the correction collar 10 to automatically correct the spherical aberration, and obtain a rotation angle $\theta 1$ of the correction collar 10 in that state. In this case, the PC 20 may compare the contrast of an image of the sample S for each rotation angle of the correction collar 10, and determine a state in which an image with the highest contrast is obtained to be a state in which the spherical aberration has been corrected. This point is similar in the following processes of correcting the spherical aberration.

The PC 20 calculates chromatic aberration $\Delta ca1$ between two wavelengths, i.e., the wavelength $\lambda 1$ and the second wavelength $\lambda 2$ (step S23 of FIG. 5). The chromatic aberration between two wavelengths is chromatic aberration generated between the light L1 having the first wavelength $\lambda 1$ and the light L2 having the second wavelength $\lambda 2$, and represents a distance in a Z direction between a condensing position of the light L1 and a condensing position of the light L2. Here, the PC 20 calculates the chromatic aberration $\Delta ca1$ between two wavelengths from the initial conditions (the first wavelength $\lambda 1$, the second wavelength $\lambda 2$, the refractive index n21, the refractive index n22, and the like) that has been set in step S10. A method for calculating chromatic aberration in a state in which a refractive index up to a condensing position of light is known is publicly known, and therefore a detailed description of the method for calculating the chromatic aberration is omitted.

Figure 8B:
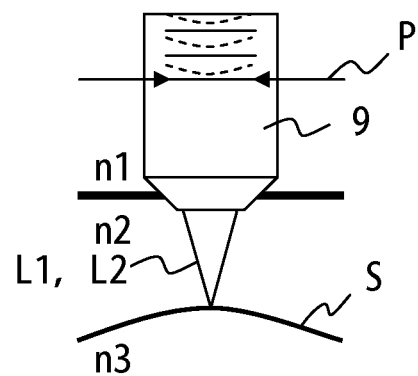
FIG. 8B illustrates a state in which chromatic aberration has been corrected on the surface of a sample.

The PC 20 corrects chromatic aberration for the light L2 having the second wavelength $\lambda 2$ (step S24 of FIG. 5). Here, the PC 20 controls the laser 1 to emit the light L2 having the second wavelength $\lambda 2$. Further, the PC 20 controls the wavefront modulator 2 to move the condensing position of the light L2 in the optical axis direction. More specifically, the wavefront modulator 2 modulates a wavefront of the light L2 so as to move the condensing position of the light L2 along the optical axis in a direction approaching the condensing position of the light L1 by a distance represented by the chromatic aberration $\Delta ca1$ that has been calculated in step S23. As a result, as illustrated in FIG. 8B, the condensing position of the light L1 and the condensing position of the light L2 coincide with the surface of the sample S, and the chromatic aberration between two wavelengths is corrected.

The PC 20 corrects spherical aberration generated in the light L2 having the second wavelength $\lambda 2$ (step S25 of FIG. 5). In this step, in a state in which the laser 1 continuously emits the light L2 having the second wavelength $\lambda 2$, a user rotates the correction collar 10 while viewing an image of the sample S displayed on a monitor so as to correct the spherical aberration. Then, the user inputs a rotation angle $\theta 2$ of the correction collar 10 in a state in which the spherical aberration has been corrected to the PC 20 by using an input device.

Finally, the PC 20 records setting information of the microscope system 100 on the surface of the sample S (step S26 of FIG. 5), and finishes the observation preprocess on the surface of the sample S. Here, the PC 20 associates the rotation angle $\theta 1$ of the correction collar 10 for the light L1 obtained in step S22, the rotation angle $\theta 2$ of the correction collar 10 for the light L2 obtained in step S25, and the chromatic aberration $\Delta ca1$ calculated in step S23 with a relative position (Z position) in the optical axis direction of the objective 9 with respect to the sample S, and records them in a recording unit provided in the PC 20.

When the observation preprocess on the surface of the sample S has been finished, the PC 20 moves the Z position (step S30 of FIG. 4). Here, the PC 20 controls the revolver 8 to relatively move the objective 9 in the optical axis direction with respective to the sample S. More specifically, the PC 20 controls the revolver 8 such that the objective 9 approaches the sample S by the pitch Δz that has been set in step S10. As a result, as illustrated in FIG. 8C, the condensing positions of the light L1 and the light L2 move inside the sample S.

Then, the PC 20 performs an observation preprocess in a Z position after the movement (step S40 of FIG. 4). Specifically, seven processes illustrated in FIG. 6 are performed.

The PC 20 corrects spherical aberration generated in the light L1 having the first wavelength λ1 (step S41 of FIG. 6). Here, the PC 20 controls the laser 1 to emit the light L1 having the first wavelength λ1. In a state in which the laser 1 is emitting the light L1 having the first wavelength λ1, a user rotates the correction collar 10 while viewing an image of the sample S displayed on a monitor, and corrects the spherical aberration. Then, the user inputs a rotation angle θ1 of the correction collar 10 in a state the spherical aberration has been corrected to the PC 20 by using an input device.

The PC 20 corrects spherical aberration generated in the light L2 having the second wavelength λ2 (step S42 of FIG. 6). Here, the PC 20 controls the laser 1 to emit the light L2 having the second wavelength λ2. In a state in which the laser 1 is emitting the light L2 having the second wavelength λ2, a user rotates the correction collar 10 while viewing an image of the sample S displayed on a monitor, and corrects the spherical aberration. Then, the user inputs a rotation angle θ2a of the correction collar 10 in a state in which the spherical aberration has been corrected to the PC 20 by using an input device.

The PC 20 calculates, for each wavelength, an average refractive index of a medium between the objective 9 and a condensing position of light emitted from the objective 9 (step S43 of FIG. 6).

Figure 9A:
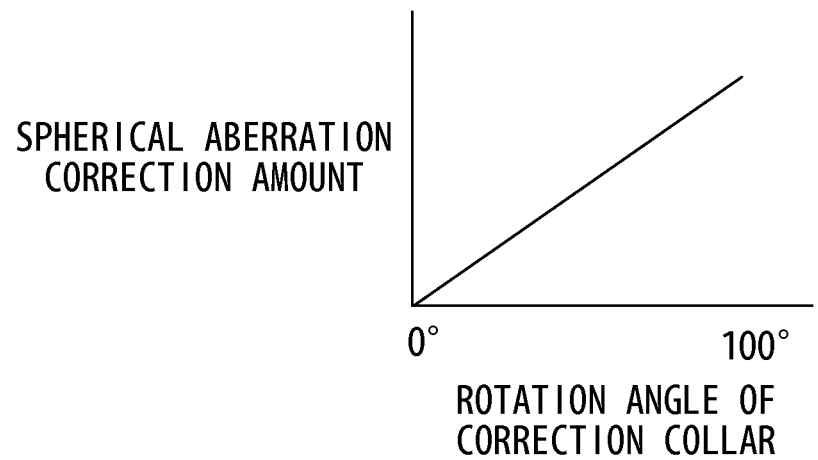
FIG. 9A illustrates a relationship between a rotation angle of a correction collar and a spherical aberration correction amount.
Figure 9B:
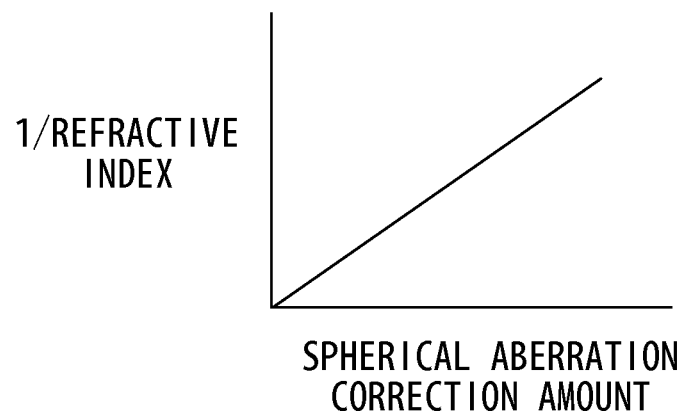
FIG. 9B illustrates a relationship between a spherical aberration correction amount and an average refractive index.

Here, the PC 20 first calculates an amount of spherical aberration for the light L1 corrected by the correction collar 10 from the rotation angle θ1 of the correction collar 10 obtained in step S41. A correction amount of the spherical aberration is uniquely calculated for a rotation angle, since the rotation angle of the correction collar 10 and the correction amount of the spherical aberration have a proportional relation as illustrated in FIG. 9A, and an inclination of the proportional relation is known from information of the objective 9 that has been set as the initial conditions in step S10. Next, the PC 20 calculates an average refractive index of a medium between the objective 9 and a condensing position of the light L1 from the calculated correction amount of the spherical aberration. The average refractive index of the medium is uniquely calculated for the correction amount of the spherical aberration, since the correction amount of the spherical aberration and the reciprocal of the average refractive index of the medium have a proportional relation as illustrated in FIG. 9B, and an inclination of the proportional relation is known from the information of the objective 9 that has been set as the initial conditions in step S10. By the similar procedure, an amount of spherical aberration for the light L2 corrected by the correction collar 10 (i.e. correction amount of the spherical aberration) is calculated from the rotation angle θ2a of the correction collar 10 obtained in step S42, and an average refractive index of a medium between the objective 9 and a condensing position of the light L2 is calculated from the calculated correction amount of the spherical aberration.

As a result, an average refractive index at each wavelength of a medium between the objective 9 and a condensing position of light emitted from the objective 9 is calculated on the basis of the correction amount of the spherical aberration by the correction collar 10.

In step S43, the average refractive index of the medium between the objective 9 and the condensing position is calculated, but an average refractive index of the sample S from the surface of the sample S to the condensing position may be further calculated. A ratio of the immersion liquid and the sample S that are filled between the objective 9 and the condensing position is calculated from a working distance WD and a pitch Δz that have been set in step S10. Therefore, the PC 20 may calculate, for each wavelength, the average refractive index of the sample S from the surface of the sample S to the condensing position on the basis of the average refractive index of the medium between the objective 9 and the condensing position, the refractive index of the immersion liquid (the refractive index n21 or the refractive index n22), the working distance WD, the pitch Δz, and the wavelength of light (the wavelength λ1 or the wavelength λ2).

The PC 20 calculates chromatic aberration Δca2 between two wavelengths, i.e., the first wavelength λ1 and the second wavelength λ2 (step S44 of FIG. 6). Here, the PC 20 calculates the chromatic aberration Δca2 between the first wavelength λ1 and the second wavelength λ2 on the basis of the average refractive index of the medium for the light L1 having the wavelength λ1 that has been calculated in step S43 and the average refractive index of the medium for the light L2 having the wavelength λ2 that has been calculated in step S43. More specifically, the PC 20 calculates the chromatic aberration generated between the wavelength λ1 and the wavelength λ2 from the initial conditions set in step S10 (the first wavelength λ1, the second wavelength λ2, the working distance WD, the lens data, and the like) and the average refractive index for each wavelength calculated in step S43. Since the refractive index up to the condensing position of the light has been calculated in step S43, in step S44, chromatic aberration can be calculated with a method similar to that in step S23.

Figure 8D:
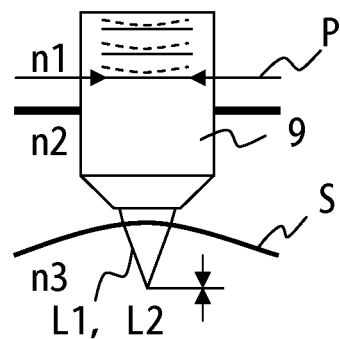
FIG. 8D illustrates a state in which chromatic aberration has been corrected inside a sample.

The PC 20 corrects chromatic aberration for the light L2 having the second wavelength λ2 (step S45 of FIG. 6). Here, the PC 20 controls the laser 1 to emit the light L2 having the second wavelength λ2. Further, the PC 20 controls the wavefront modulator 2 to move a condensing position of the light L2 in the optical axis direction. More specifically, the wavefront modulator 2 modulates a wavefront of the light L2 such that the condensing position of the light L2 moves in a direction approaching the condensing position of the light L1 along the optical axis by a distance represented by the chromatic aberration Δca2 calculated in step S44. As a result, as illustrated in FIG. 8D, the condensing position of the light L1 coincides with the condensing position of the light L2 inside the sample S, and the chromatic aberration between two wavelengths is corrected.

The PC 20 corrects spherical aberration generated in the light L2 having the second wavelength λ2 (step S46 of FIG. 6). Here, in a state in which the laser 1 continuously emits the light L2 having the second wavelength λ2, a user rotates the correction collar 10 while viewing an image of the sample S displayed on a monitor, and corrects the spherical aberration. Then, the user inputs a rotation angle θ2b of the correction collar 10 in a state in which the spherical aberration has been corrected to the PC 20 using an input device.

Finally, the PC 20 records setting information of the microscope system 100 in a current Z position (inside the sample S) (step S47 of FIG. 6), and finishes the observation preprocess in the Z position after the movement. Here, the PC 20 associates the rotation angle θ1 of the correction collar 10 for the light L1 obtained in step S41, the rotation angle θ2b of the correction collar 10 for the light L2 obtained in step S46, the chromatic aberration Δca2 calculated in step S44 with a relative position (Z position) in the optical axis direction of the objective 9 with respect to the sample S, and records them in a recording unit provided in the PC 20.

When the observation preprocess in the Z position after the movement has been finished, the PC 20 determines whether the Z position has been moved to all of the scheduled positions (step S50 of FIG. 4). Here, the PC 20 performs this determination on the basis of, for example, the current Z position, the thickness d and the pitch Δz of the sample that have been set in step 10. When the PC 20 determines that the Z position has not been moved to all of the scheduled positions, the PC 20 repeats the processes of step S30 though step S50. On the other hand, when the PC 20 determines that the Z position has been moved to all of the scheduled positions, the PC 20 finishes the observation preprocess illustrated in FIG. 4.

As described above, in the microscope system 100, the PC 20 performs the observation preprocess illustrated in FIG. 4 so as to obtain the setting for correcting the chromatic aberration generated between the first wavelength λ1 and the second wavelength λ2 in each position on the surface of the sample S and inside the sample S.

When the PC has finished the observation preprocess illustrated in FIG. 4, the PC 20 starts an observation process illustrated in FIG. 7. First, the PC 20 obtains initial conditions input by a user, and sets the obtained initial conditions (step S60 of FIG. 7). Here, a plane to be observed (Z position) of the sample S and the like are set as the initial conditions. A plurality of Z positions may be set.

The PC 20 moves the Z position that has been set in step S60 (step S70 of FIG. 7). Here, the PC 20 controls the revolver 8 to relatively move the objective 9 in the optical axis direction with respect to the sample S, and moves the Z position.

The PC 20 sets setting information according to the Z position after the movement of the Z position (step S80 of FIG. 7). Here, the PC 20 reads the setting information according to the Z position (rotation angles of the correction collar 10 for the light L1 and the light L2, and chromatic aberration generated between the light L1 and the light L2) from the recording unit, and sets the information.

The PC 20 obtains images at the first wavelength and the second wavelength (step S90 of FIG. 7). Here, the PC 20 first rotates the correction collar 10 so as to have the rotation angle of the correction collar 10 for the light L1 set in step S80, and then the PC makes the laser 1 emit the light L1 having the first wavelength λ1 and obtains an image of the sample S. Further, the PC 20 records the obtained image in the recording unit. Next, the PC 20 rotates the correction collar 10 so as to have a rotation angle of the correction collar 10 for the light L2 set in step S80, and sets a modulation pattern of the wavefront modulator 2 so as to correct the chromatic aberration set in step S80. Then, the PC 20 makes the laser 1 emit the light L2 having the second wavelength λ2, and obtains an image of the sample S. Further, the PC 20 records the obtained image in the recording unit. An example in which the PC 20 controls the rotation of the correction collar 10 has been provided, but the correction collar 10 may be rotated manually.

When the images have been obtained, the PC 20 determines whether the Z position has been moved to all of the scheduled positions set in step S60 (step S100 of FIG. 7). When the PC determines that the Z position has not been moved to all of the scheduled positions, the PC 20 repeats the processes of step S70 through step S100. On the other hand, when the PC 20 determines that the Z position has been moved to all of the scheduled positions, the PC 20 finishes the observation process illustrated in FIG. 7.

The microscope system 100 according to this embodiment enables correcting chromatic aberration generated between wavelengths in each Z position even when a refractive index of a sample S is unknown. Therefore, condensing positions of light beams having two different wavelengths can be maintained inside an arbitrary sample S, and the same position inside the arbitrary sample S can be observed with light beams having different wavelengths. In addition, the microscope system 100 according to this embodiment enables obtaining an average refractive index of a sample S from a surface of the sample S to a condensing position.

A method for collectively calculating chromatic aberration in each Z position before the observation of the sample S is started is illustrated in FIG. 4 to FIG. 7; however, the chromatic aberration may be calculated every time a Z position is changed after the observation of the sample S is started, and the calculated chromatic aberration may be corrected every time.

In addition, an example in which the chromatic aberration generated between the first wavelength and the second wavelength is corrected by modulating the condensing position of the light having the second wavelength λ2 is illustrated in FIG. 4 to FIG. 7; however, the microscope system 100 may correct the chromatic aberration by modulating a condensing position of the light having the first wavelength λ1. Further, the microscope system 100 may correct the chromatic aberration by modulating the condensing positions of both of the lights having the two wavelengths, instead of modulating the condensing position of the light having either one of the two wavelengths.

In addition, an example in which chromatic aberration generated between two wavelengths is corrected is provided in FIG. 4 to FIG. 7; however, the microscope system 100 may correct chromatic aberration generated among three or more wavelengths. In this case, as an example, chromatic aberration from a reference wavelength may be calculated for each wavelength, and a condensing position of light having each wavelength may be made to coincide with a condensing position of light having the reference wavelength.

In addition, an example in which chromatic aberration is corrected for each Z position is provided in FIG. 4 to FIG. 7; however, the microscope system 100 may calculate and correct chromatic aberration in each Z position and in each XY positions controlled by the galvano-scanner 4.

FIG. 10 is a flowchart of a process of measuring a refractive index of a sample S performed in the microscope system 100 according to this embodiment. With reference to FIG. 10, a method for measuring the refractive index of the sample S is described below.

When a refractive index measurement process is started, the PC 20 obtains initial conditions input by a user, and sets the obtained initial conditions (step S110 of FIG. 10). Here, as the initial conditions, a wavelength λ of light applied to the sample S, a refractive index n2 of immersion liquid at the wavelength λ, information of a used objective (e.g., a working distance WD or lens data), a pitch Δz at the time of moving a Z position in an optical axis direction, a thickness d of a sample, and the like are set.

Next, the PC 20 makes a condensing position of light having the wavelength λ coincide with a surface of the sample S (step S120 of FIG. 10, a first condensing position movement step). Here, the PC 20 makes the condensing position coincide with the surface of the sample S in a manner similar to step S21 of FIG. 5). Then, the PC 20 repeats the processes of step S130 through step S160.

First, the PC 20 moves a Z position (step S130 of FIG. 10, a second condensing position movement step). Here, the PC 20 moves the Z position in a manner similar to step S21 of FIG. 5. More specifically, the PC 20 controls the revolver 8 such that the objective 9 approaches the sample S by the pitch Δz set in step S110.

Then, the PC 20 corrects spherical aberration inside the sample S generated in the light having the wavelength λ (step S140 of FIG. 10, a spherical aberration correction step). Here, the PC 20 controls the laser 1 to emit the light having the wavelength λ. In a state in which the laser 1 is emitting the light having the wavelength λ, a user rotates the correction collar 10 while viewing an image of the sample S displayed on a monitor, and corrects the spherical aberration. Then, the user inputs a rotation angle θ of the correction collar 10 in a state in which the spherical aberration has been corrected to the PC 20 by using an input device.

Then, the PC 20 calculates an average refractive index of the sample S from a surface of the sample S to a condensing position of light emitted from the objective 9 (step S150 of FIG. 10, a refractive index calculation step). Here, the PC 20 first calculates an average refractive index of a medium between the objective 9 and the condensing position on the basis of the correction amount of the spherical aberration by the correction collar 10 in step S140 in a manner similar to step S43 of FIG. 6 (a first refractive index calculation step). Further, the PC 20 calculates an average refractive index of the sample S from the surface of the sample S to the condensing position on the basis of a ratio of immersion liquid and the sample S that are filled between the objective 9 and the condensing position and the average refractive index of the medium between the objective 9 and the condensing position (a second refractive index calculation step). The ratio is calculated from the working distance WD and the pitch Δz.

The PC 20 calculates an average refractive index of the sample S between two condensing positions before and after the movement of the Z position (step S160 of FIG. 10). Here, an average refractive index of the sample S between the condensing positions before and after the movement of the Z position is calculated on the basis of the two average refractive index calculated in step S150 before and after the movement of the Z position in step S130 (i.e., an average refractive index of the sample S from the surface of the sample S to the condensing position before the movement of the Z position and an average refractive index of the sample S from the surface of the sample S to the current condensing position after the movement of the Z position) and the pitch Δz.

The PC 20 determines whether the Z position has been moved to all of the scheduled positions (step S170 of FIG. 10). Here, the PC 20 performs this determination on the basis of, for example, the current Z position, the thickness d of the sample and the pitch Δz set in step S110, and the like. When the PC 20 determines that the Z position has not been moved to all of the scheduled positions, the PC 20 repeats the processes of step S130 through step S170. On the other hand, when the PC 20 determines that the Z position has been moved to all of the scheduled positions, the PC 20 finishes the refractive index measurement process illustrated in FIG. 10.

In the refractive index measurement process described above, the microscope system 100 according to this embodiment enables obtaining the distribution of the refractive index of the sample S whose refractive index is unknown. In addition, the smaller the pitch Δz, the more detailed distribution of the refractive index of the sample S can be obtained.

In FIG. 10, an example of measuring a refractive index for a specific wavelength of the sample S is provided; however, the microscope system 100 may repeat the processes in FIG. 10 for each wavelength and measure refractive indexes for a plurality of wavelengths.

In addition, in FIG. 10, an example of calculating the distribution of a refractive index in a Z direction is provided; however, the microscope system 100 may calculate the distribution of a refractive index in XY directions controlled by the galvano-scanner 4 in addition to the distribution of the refractive index in the Z direction.

Embodiment 2

FIG. 11 illustrates a configuration of a microscope system 101 according to this embodiment. The microscope system 101 illustrated in FIG. 11 is different from the microscope system 100 according to Embodiment 1 in that the microscope system 101 illustrated in FIG. 11 includes a deformable mirror 14, a pupil relay optical system 17, and a mirror 18, instead of a correction collar 10. The other configuration is similar to that of the microscope system 100.

The deformable mirror 14 is a spherical aberration corrector that corrects spherical aberration caused by a difference between a refractive index of a medium between an objective 9 and a sample S and a refractive index of the sample S by modulating a wavefront of a laser beam. The deformable mirror 14 is arranged in a position optically conjugate to a pupil position of the objective 9. More specifically, the deformable mirror 14 is arranged in a position in which an image of a galvano-scanner 4 is projected by the pupil relay optical system 17 and the mirror 18, as illustrated in FIG. 11.

In the microscope system 101 according to this embodiment, the deformable mirror 14 functions as the spherical aberration corrector instead of the correction collar 10, and therefore chromatic aberration generated between wavelengths in each Z position can be corrected even when a refractive index of the sample S is unknown, similarly to the microscope system 100 according to Embodiment 1. Therefore, condensing positions of light beams having two different wavelengths can be maintained inside an arbitrary sample S, and the same position inside the arbitrary sample S can be observed with light beams having different wavelengths. In addition, similarly to the microscope system 100 according to Embodiment 1, the microscope system 101 according to this embodiment enables obtaining the distribution of a refractive index of a sample S whose refractive index is unknown.

Embodiment 3

Figure 12:
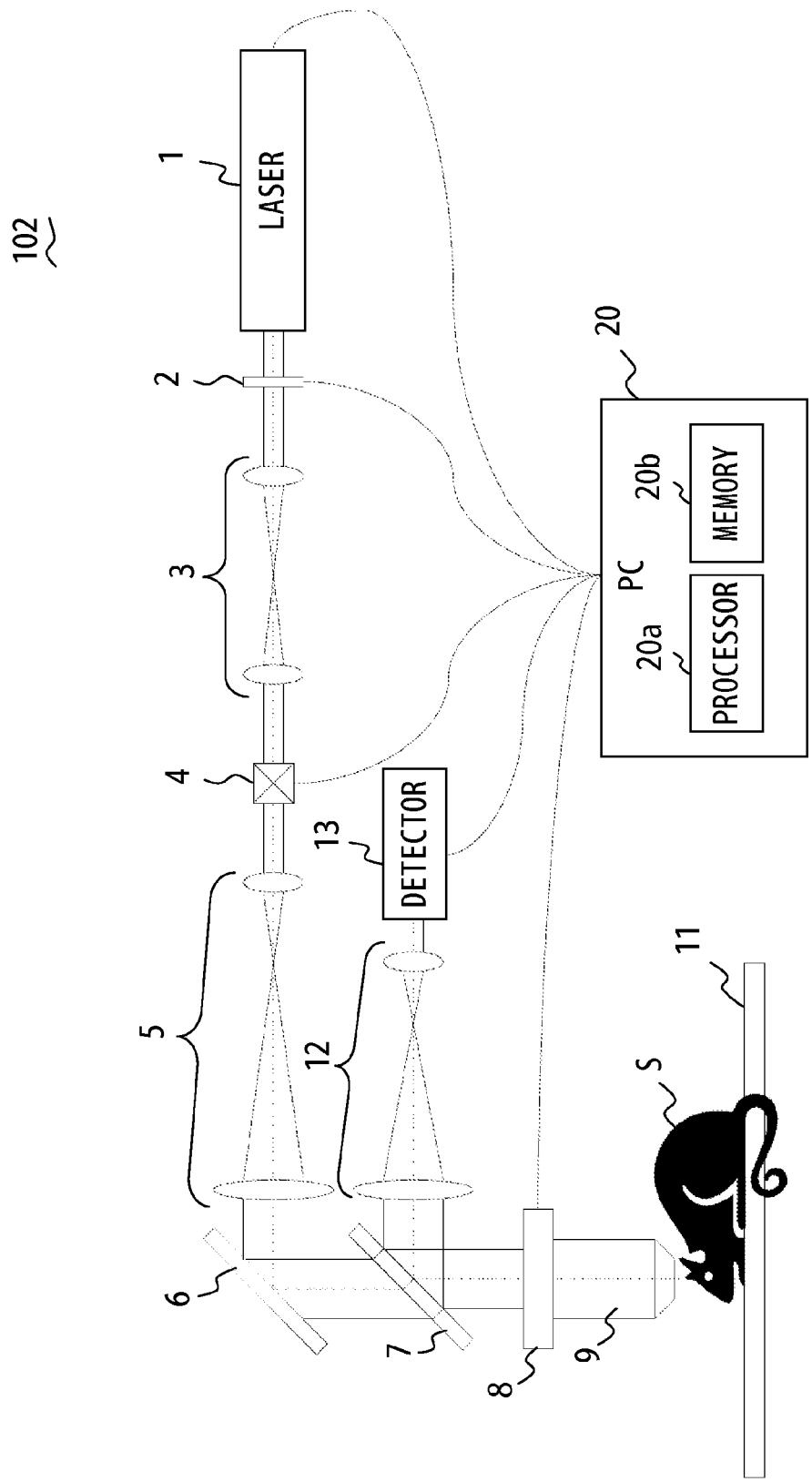
FIG. 12 illustrates a configuration of a microscope system according to Embodiment 3 of the present invention.

FIG. 12 illustrates a configuration of a microscope system 102 according to this embodiment. The microscope system 102 illustrated in FIG. 12 is different from the microscope system 100 according to Embodiment 1 in that a correction collar 10 is omitted. The other configuration is similar to that of the microscope system 100.

In the microscope system 102, a wavefront modulator 2 modulates a wavefront of a laser beam so as to correct spherical aberration at the time of correcting chromatic aberration. Namely, in the wavefront modulator 2, a modulation pattern that has been formed by superposing a modulation pattern for correcting chromatic aberration on a modulation pattern for correcting spherical aberration is set.

In the microscope system 102 according to this embodiment, the wavefront modulator 2 functions as a spherical aberration corrector, instead of the correction collar 10, and therefore chromatic aberration generated between wavelengths in each Z position can be corrected even when a refractive index of a sample S is unknown, similarly to the microscope system 100 according to Embodiment 1. Therefore, condensing positions of light beams having different wavelengths can be maintained inside an arbitrary sample S, and the same position inside the arbitrary sample S can be observed with the light beams having different wavelengths. In addition, similarly to the microscope system 100 according to Embodiment 1, the microscope system 102 according to this embodiment enables obtaining the distribution of a refractive index of a sample S whose refractive index is unknown.

Embodiment 4

Figure 13:
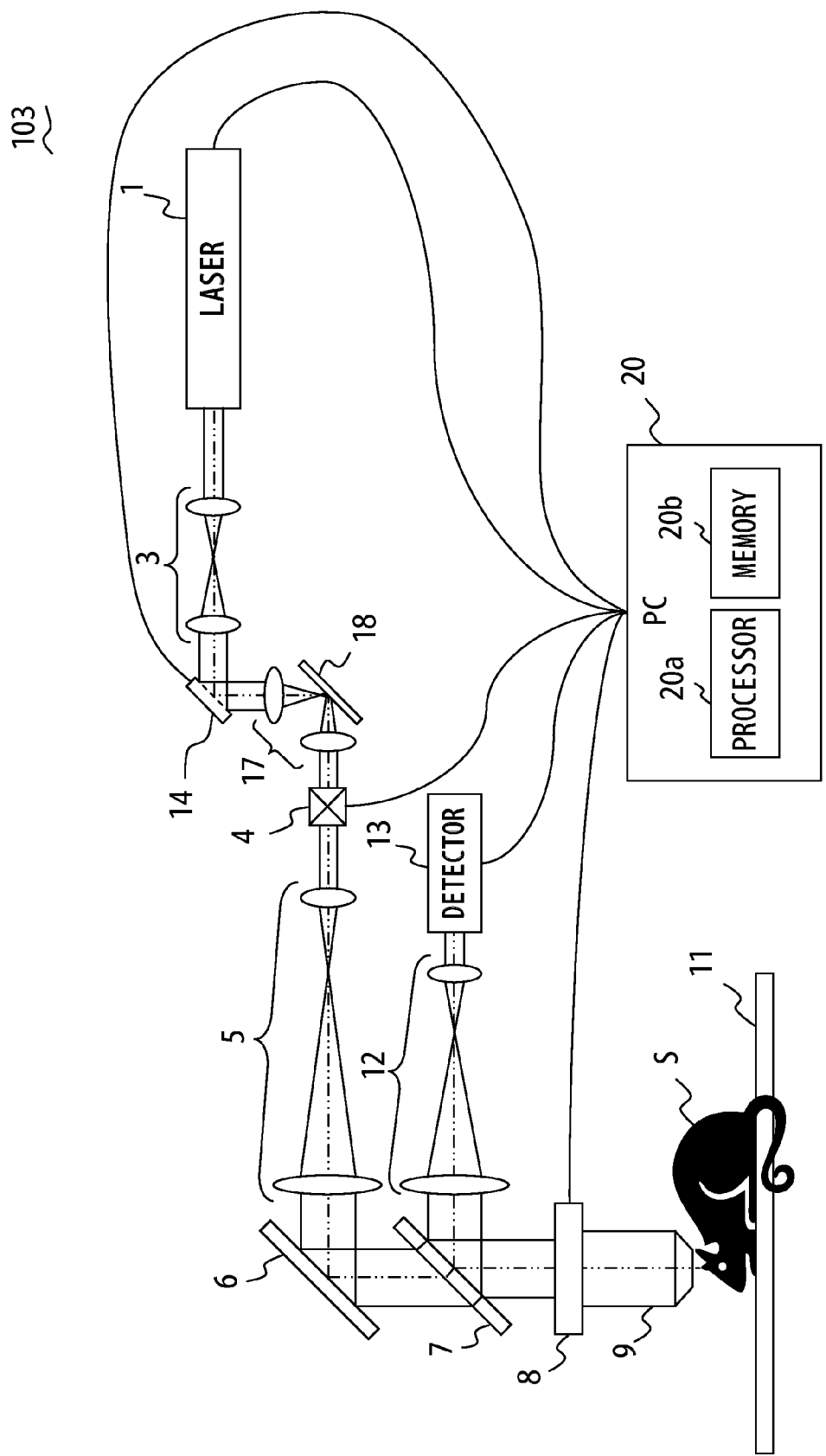
FIG. 13 illustrates a configuration of a microscope system according to Embodiment 4 of the present invention.

FIG. 13 illustrates a configuration of a microscope system 103 according to this embodiment. The microscope system 103 illustrated in FIG. 13 is different from the microscope system 100 according to Embodiment 1 in that the microscope system 103 includes a deformable mirror 14, a pupil relay optical system 17, and a mirror 18, instead of a wavefront modulator 2 and a correction collar 10. The other configuration is similar to that of the microscope system 100.

The deformable mirror 14 is a spherical aberration corrector that corrects spherical aberration caused by a difference between a refractive index of a medium between an objective 9 and a sample S and a refractive index of the sample S by modulating a wavefront of a laser beam. In addition, the deformable mirror 14 is also a chromatic aberration corrector that corrects chromatic aberration by modulation the wavefront of the laser beam. The deformable mirror 14 is arranged in a position optically conjugate to a pupil position of the objective 9. More specifically, the deformable mirror 14 is arranged in a position in which an image of a galvano-scanner 4 is projected by the pupil relay optical system 17 and the mirror 18, as illustrated in FIG. 13.

In the microscope system 103, the deformable mirror 14 modulates the wavefront of the laser beam so as to correct the spherical aberration at the time of correcting the chromatic aberration. Namely, in the deformable mirror 14, a modulation pattern that has been formed by superposing a modulation pattern for correcting the chromatic aberration on a modulation pattern for correcting the spherical aberration is set.

In the microscope system 103 according to this embodiment, the deformable mirror 14 functions as a spherical aberration corrector, instead of the correction collar 10, and the deformable mirror 14 functions as a chromatic aberration corrector, instead of the wavefront modulator 2, and therefore chromatic aberration generated between wavelengths in each Z position can be corrected even when a refractive index of a sample S is unknown, similarly to the microscope system 100 according to Embodiment 1. Therefore, condensing positions of light beams having different wavelengths can be maintained inside an arbitrary sample S, and the same position inside the arbitrary sample S can be observed with the light beams having different wavelengths. In addition, similarly to the microscope system 100 according to Embodiment 1, the microscope system 103 according to this embodiment enables obtaining the distribution of a refractive index of a sample S whose refractive index is unknown.

Embodiment 5

FIG. 14 illustrates a configuration of a microscope system 104 according to this embodiment. The microscope system 104 illustrated in FIG. 14 is different from the microscope system 100 according to Embodiment 1 in that the microscope system 104 includes a plurality of lasers (a laser 1a and a laser 1b), a plurality of wavefront modulators (a wavefront modulator 2a and a wavefront modulator 2b), a plurality of beam expanders (a beam expander 3a and a beam expander 3b), a mirror 15, and a dichroic mirror 16, instead of a laser 1, a wavefront modulator 2, and a beam expander 3. The other configuration is similar to that of the microscope system 100.

In the microscope system 104 according to this embodiment, the wavefront modulator 2a modulates a wavefront of a laser beam emitted from the laser 1a, and the wavefront modulator 2b modulates a wavefront of a laser beam emitted from the laser 1b so as to correct chromatic aberration generated between the laser beam emitted from the laser 1a and the laser beam emitted from the laser 1b.

Accordingly, in the microscope system 104 according to this embodiment, similarly to the microscope system 100 according to Embodiment 1, chromatic aberration generated between wavelengths in each Z position can be corrected even when a refractive index of a sample S is unknown. Therefore, condensing positions of light beams having different wavelengths can be maintained inside an arbitrary sample S, and the same position inside the arbitrary sample S can be observed with the light beams having different wavelengths. In addition, similarly to the microscope system 100 according to Embodiment 1, the microscope system 104 according to this embodiment enables obtaining the distribution of a refractive index of a sample S whose refractive index is unknown.

Each of the embodiments described above gives a specific example of the present invention in order to easily understand the invention, and the present invention is not limited to these embodiments. Various modifications or variations of a microscope system and a method for measuring a refractive index according to these embodiments can be made without departing from the spirit of the present invention specified in the claims.

For example, the embodiments described respectively give an example in which a microscope system includes a two-photon excitation microscope; however, the microscope system may include another multi-photon excitation microscope, such as a three-photon excitation microscope. In addition, a microscope included in the microscope system may be all types of microscope for observing the inside of a sample, and the microscope system may include a microscope other than a multi-photon excitation microscope, such as a confocal microscope.

Further, the embodiments described above provide an example in which a galvano-scanner is used as a scanner, but a resonant scanner may be used.

What is claimed is:

1. A microscope system comprising:
   a wavefront modulator that modulates a wavefront of light from a light source;
   an objective that irradiates a sample with light whose wavefront has been modulated by the wavefront modulator;
   a spherical aberration corrector that corrects spherical aberration caused by a difference between a refractive index of a medium between the objective and the sample and a refractive index of the sample;
   a refractive index calculator that calculates, for each wavelength of the light from the light source, an average refractive index of a medium between the objective and a condensing position of light emitted from the objective on the basis of an amount of the spherical aberration corrected by the spherical aberration corrector; and
   a controller that controls the wavefront modulator to correct chromatic aberration calculated on the basis of the average refractive index for each wavelength that has been calculated by the refractive index calculator.

2. The microscope system according to claim 1, further comprising:
   a chromatic aberration calculator that calculates chromatic aberration generated between wavelengths on the basis of the average refractive index for each wavelength that has been calculated by the refractive index calculator, wherein the controller controls the wavefront modulator to correct the chromatic aberration calculated by the chromatic aberration calculator.

3. The microscope system according to claim 1, further comprising:

a Z scanner that relatively moves the objective in an optical axis direction with respect to the sample, and changes the condensing position of the light emitted from the objective, wherein the refractive index calculator calculates the average refractive index of the medium between the objective and the condensing position of the light emitted from the objective on the basis of the amount of the spherical aberration corrected by the spherical aberration corrector, for each of the condensing positions changed by the Z scanner and for each wavelength of the light from the light source.

4. The microscope system according to claim 1, wherein the wavefront modulator modulates a wavefront of light having one of two wavelengths under the control of the controller such that a condensing position of the light having the one of the two wavelengths moves in an optical axis direction of the objective by a distance represented by the chromatic aberration generated between the two wavelengths that has been calculated by the refractive index calculator.

5. The microscope system according to claim 1, wherein the objective includes a correction collar that is the spherical aberration corrector.

6. The microscope system according to claim 1, further comprising:

a multi-photon excitation microscope that includes the objective, the wavefront modulator, and the spherical aberration corrector.

7. A method for measuring a refractive index of a sample with a microscope system, the method comprising:

relatively moving an objective in an optical axis direction with respect to the sample so as to make a condensing position of light emitted from the objective of the microscope system coincide with a surface of the sample;

relatively moving the objective in the optical axis direction with respect to the sample so as to move the condensing position of the light emitted from the objective inside the sample;

correcting spherical aberration inside the sample; and calculating, by a refractive index calculator of the microscope system, the refractive index of the sample between the surface of the sample and the condensing position inside the sample on the basis of an amount of the corrected spherical aberration, wherein the calculating the refractive index of the sample by the refractive index calculator comprises:

calculating an average refractive index of a medium between the objective and the condensing position inside the sample on the basis of the amount of the corrected spherical aberration; and calculating a refractive index of the sample between the surface of the sample and the condensing position inside the sample on the basis of a working distance of the objective, a movement amount of the condensing position from the surface of the sample to the inside of the sample, the calculated average refractive index, and a refractive index of a medium between the objective and the surface of the sample.

\* \* \* \* \*